United States Patent [19]

Cusic et al.

[11] 3,965,104

[45] June 22, 1976

[54] 1-(SUBSTITUTED-AMINOALKYL)-3-BENZOYL-4-HYDROXY-4-PHENYLPIPERIDINES AND RELATED COMPOUNDS

[75] Inventors: John W. Cusic, Skokie; Charles R. Ellefson, Chicago; Chi Min Woo, Skokie, all of Ill.

[73] Assignee: G. D. Searle & Co., Chicago, Ill.

[22] Filed: June 16, 1975

[21] Appl. No.: 587,401

[52] U.S. Cl....................... 260/293.64; 260/293.69; 260/293.71; 260/293.78; 424/267
[51] Int. Cl.²....................................... C07D 211/52
[58] Field of Search................. 260/293.64, 293.69, 260/293.71, 293.78

[56] References Cited
FOREIGN PATENTS OR APPLICATIONS
569,275   1/1959   Canada.......................... 260/293.64

OTHER PUBLICATIONS

Tomcufcik et al., C.A. 68: 95,699a, (1968).

*Primary Examiner*—Sherman D. Winters
*Attorney, Agent, or Firm*—John J. Kolano

[57] ABSTRACT

1-(Substituted-aminoalkyl)-3-benzoyl-4-hydroxy-4-phenylpiperidines and related compounds having antiarrhythmic activity are described herein. The 3-benzoyl compounds can be prepared by condensing the appropriate diamine with acetophenone and formaldehyde. The related 3-(α-hydroxybenzyl) compounds are prepared by reduction of the corresponding 3-benzoyl compounds.

7 Claims, No Drawings

1-(SUBSTITUTED-AMINOALKYL)-3-BENZOYL-4-HYDROXY-4-PHENYLPIPERIDINES AND RELATED COMPOUNDS

The present invention relates to a group of 1-(substituted-aminoalkyl)-3-benzoyl-4-hydroxy-4-phenylpiperidines and their corresponding 3-($\alpha$-hydroxybenzyl)analogs. More particularly, the present invention relates to a group of compounds having the general formula

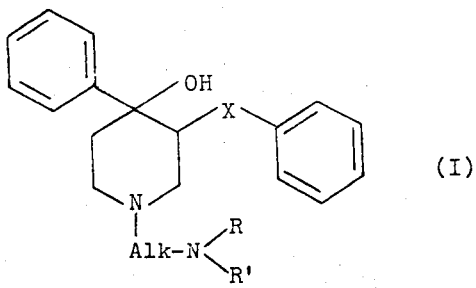

(I)

wherein X is hydroxymethylene or keto; Alk is alkylene of 2 to 6 carbon atoms, separating the nitrogen atoms attached thereto by at least 2 carbon atoms; and NRR' is selected from the group consisting of di(lower alkyl)amino, pyrrolidino, piperidino, and hexamethyleneimino.

The lower alkyl groups referred to above contain 1 to 6 carbon atoms and are exemplified by methyl, ethyl, propyl, isopropyl and the like. The alkylene groups referred to above contain 2 to 6 carbon atoms and can be exemplified by groups such as ethylene, propylene, trimethylene and 1,4-pentylene.

Equivalent to the compounds of formula (I) for the purposes of this invention are the pharmaceutically acceptable acid addition and quaternary ammonium salts thereof. Such acid addition salts can be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids. Similarly, the quaternary ammonium salts can be derived from a variety of organic esters of sulfuric hydrohalic and aromatic sulfonic acids. Among such esters are methyl chloride and bromide, ethyl chloride, propyl chloride, butyl chloride, isobutyl chloride, benzyl chloride and bromide, phenethyl bromide, naphthylmethyl chloride, dimethyl sulfate, methyl benzenesulfonate, ethyl toluenesulfonate, ethylene chlorohydrin, propylene chlorohydrin, allyl bromide, methallyl bromide and crotyl bromide. Also equivalent to the compounds of formula (I) are solvates thereof in which the solvents are present in biologically insignificant amounts.

The compounds of this invention are useful because of their pharmacological properties. In particular, they possess activity as anti-arrhythmic agents. Thus, they bring about a return to normal heart rhythm in animals in which the heart rhythm has become irregular.

The anti-arrhythmic utility of the instant compounds is evident from the results of a standardized test for their capacity to slow the ventricular tachycardia induced by aconitine in the isolated rabbit heart. The procedure is essentially that described by Lucchesi [*J. Pharmacol. Exp. Therap.*, 137, 291 (1962)], modified in certain particulars as follows: Hearts are obtained from adult albino rabbits of either sex and perfused in apparatus molded after that devised by Anderson and Craver [*J. Pharmocol. Exp. Therap.*, 93, 135 (1948)]. The composition of the perfusion solution is the same as Lucchesi's, but the volume is increased to 200 ml. and the temperature lowered to 28°C. Aconitine (ordinarily as the nitrate) is administered as soon as the heart beat is regular and the EKG pattern normal, the dose being so selected as to at least double the rate. Typically, 0.05 ml. of 0.1% aconitine nitrate in physiological saline is injected. EKG's are recorded at 5 minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline is mixed with the perfusion solution. Ten minutes later a like amount is introduced, followed after a further 10 minutes by double the first amount. Final concentration of compound in the perfusion solution is thus 40 mg. per liter. Recording of EKG's is continued at 5 minute intervals throughout this time and for 10 minutes thereafter. A compound is considered anti-arrhythmic if, at any time during the 30 minutes immediately following initial administration in at least half of a minimum of two tests, it reduces by 50% or more the rate recorded 10 minutes after onset of tachycardia. Among the compounds of this invention which have been found particularly active in this test are the representative compounds 1-(3-diethylaminopropyl)-3-benzoyl-4-hydroxy-4-phenylpiperidine and 1-(3-piperidinopropyl)-3-($\alpha$-hydroxybenzyl)-4-hydroxy-4-phenylpiperidine.

A further test demonstrating the anti-arrhythmic utility of the present compounds is as follows:

Male mongrel dogs are connected to a physiograph to follow heart and blood action. At the onset of the testing, an initial dose of 40 mcg./kg. ouabain is administered intraveneously in a saline solution. This is followed 30 minutes later by a dose of 20 mcg./kg. of ouabain and, at 15 minute intervals, by a dose of 10 mcg./kg. of ouabain until ventricular arrhythmia occurs and persists for 20 minutes. Then, a saline solution of test compound is administered at a dose of 5 mg./kg. If the heart action does not become normal, additional test compound is administered at a dose of 5 mg./kg. at 15 minute intervals until heart action becomes normal or until the total dose of test compound administered is 20 mg./kg. The procedure is run in at least two dogs. A compound is considered anti-arrhythmic if it causes a return to normal heart action for a period of 15 minutes or more in half or more of the dogs tested at a dose of 20 mg./kg. or less. An additional compound which shows activity in this test is 1-(3-piperidinopropyl)-3-($\alpha$-hydroxybenzyl)-4-hydroxy-4-phenylpiperidine.

In view of their potent pharmacological properties, the compounds of this invention can be combined with pharmaceutical carriers and administered in a variety of well-known pharmaceutical forms suitable for oral or parenteral administraton.

Certain of the compounds of this invention, i.e., compounds wherein X is keto, are additionally useful in the synthesis of other anti-arrhythmic agents. The synthesis and properties of these anti-arrhythmic agents are described in our copending application Ser. No. 587,405, filed June 16, 1975.

The 3-benzoyl compounds of the present invention are conveniently prepared by condensing the appropriate diamine of the formula

wherein Alk and NRR' are defined as hereinabove, with acetophenone and formaldehyde. This reaction is most conveniently conducted in an organic solvent. Suitable solvents include aromatic hydrocarbons such as benzene and toluene, high boiling ethers such as dioxane, lower alkanols such as methanol and ethanol, and dimethylformamide and dimethylsulfoxide. Time and temperature are not critical factors for the conduct of the reaction, typical times varying from a few hours to several days, and typical temperatures being in the range of room temperature to reflux.

The 3-(α-hydroxybenzyl) compounds are prepared by reduction of the corresponding keto compound of the formula

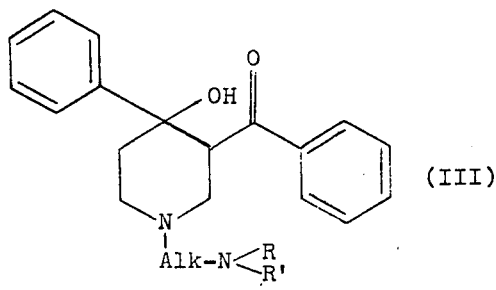

wherein Alk and NRR' are defined as hereinabove. Suitable reducing agents include aluminum hydride, sodium borohydride, sodium cyanoborohydride, and lithium perhydro-9b-borophenalylhydride. A particularly preferred reducing agent is aluminum hydride. The compounds may also be produced by catalytic hydrogenation of the keto compounds. Possible catalysts include platinum, Raney nickel, copper-chromium oxide, and palladium (optionally on a support). A particularly preferred catalyst is palladium. The hydrogenation is conveniently conducted in a solvent, the choice of solvent depending on the particular starting material. Generally, a wide variety of solvents, such as lower alkanols (e.g., methanol, ethanol and 2-propanol), ethers (e.g., tetrahydrofuran), water, and acetic acid can be used. The reaction is generally conducted at a temperature ranging from room temperature to 100°C., with a temperature range of room temperature to 50°–60°C. being typical. Reaction conditions such as time, temperature and pressure are not critical but generally depend on the particular reducing agent that is used.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth temperatures are given in degrees Centigrade (°C.), and relative amounts in parts by weight, except as otherwise noted.

EXAMPLE 1

To a solution of 10.2 parts of 3-dimethylaminopropylamine in 20 parts of absolute ethanol is added 17 parts by volume of concentrated hydrochloric acid. Then, 24.0 parts of acetophenone and 12.0 parts of paraformaldehyde are added, and the resulting mixture heated to reflux. The mixture is stirred and refluxed for 7 hours, and then left to stand at room temperature for about 18 hours. The solvents are removed at 50°C. under reduced pressure, leaving a semisolid that is partitioned between water and ethyl acetate. The water portion is washed once with ethyl acetate, and then made alkaline by the addition of 25 parts by volume of a 25% by weight solution of aqueous sodium hydroxide. The mixture is stirred under a nitrogen stream to remove trace ethyl acetate. During stirring, an oil separates. After stirring for 2 hours, the mixture is left standing overnight. The mixture is then cooled in an ice bath and the aqueous portion decanted to leave an oil. The residual oil is dissolved in ethyl ether, washed several times with water, and dried over anhydrous magnesium sulfate. Removal of the solvent under reduced pressure affords a tan solid. This solid is recrystallized from ethyl acetate-hexane to afford 1-(3-dimethylaminopropyl)-3-benzoyl-4-hydroxy-4-phenylpiperidine, melting at about 113.5°–115.5°C. and represented by the following structural formula.

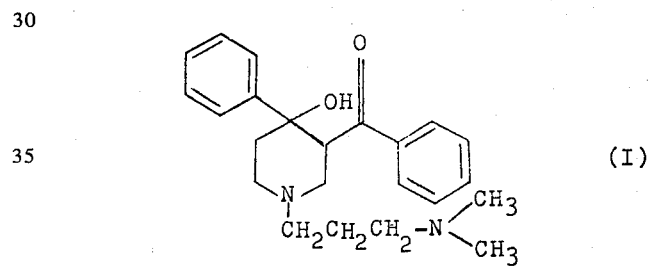

EXAMPLE 2

To a 250 parts by volume of a 4 M solution of hydrogen chloride in absolute ethanol is added 65.1 parts of 3-diethylaminopropylamine. Then, 120.0 parts of acetophenone and 60.0 parts of paraformaldehyde is added and the mixture heated to reflux. After stirring and refluxing for 24 hours, the solvent is removed under reduced pressure. The resulting oil is dissolved in water and washed with portions of ethyl ether. The solution is made alkaline (~pH 12) with 50% by weight aqueous sodium hydroxide and stirred at room temperature for 2.5 hours. During stirring an oil separates out. This oil is purified by dissolving in isopropanol, and adding to this solution a solution of hydrogen chloride in isopropanol. The resulting salt is separated by filtration and dissolved in water. The aqueous solution of the salt is extracted several times with ethyl ether, made alkaline with 50% by weight aqueous sodium hydroxide solution and then extracted with portions of ethyl acetate. The ethyl acetate fractions are combined, dried over anhydrous sodium sulfate and stripped of solvent under reduced pressure. Ethyl ether is added to the residual oil and, upon cooling, crystals precipitate. Filtration affords 1-(3-diethylaminopropyl)-3-benzoyl-4-hydroxy-4-phenylpiperidine melting at 76°–78°C.

EXAMPLE 3

Substitution of an equivalent amount of 3-piperidinopropylamine for the 3-dimethylaminopropylamine used in Example 1 and substantial repetition of the procedure detailed therein affords, 1-(3-piperidinopropyl)-3-benzoyl-4-hydroxy-4-phenylpiperidine. After recrystallization from chloroform and ethyl ether, this compound melts at about 121°–123°C., and is represented by the following structural formula.

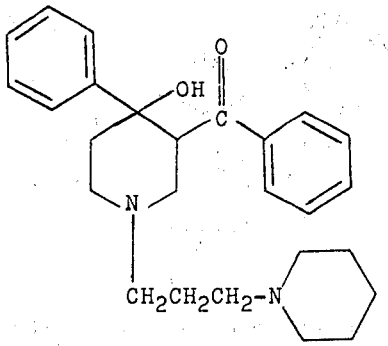

EXAMPLE 4

When an equivalent amount of 2-dimethylaminoethylamine is substituted for the 3-dimethylaminopropylamine used in Example 1 and the procedure detailed therein substantially repeated, there is obtained 1-(2-dimethylaminoethyl)-3-benzoyl-4-hydroxy-4-phenylpiperidine. This product melts at about 101°–102°C., and is represented by the following structural formula.

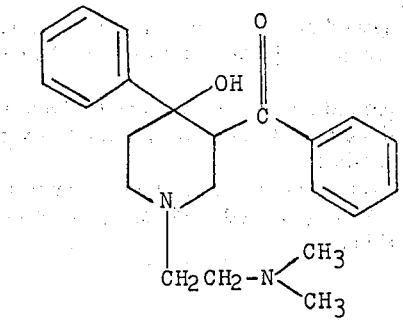

EXAMPLE 5

Substitution of an equivalent quantity of the appropriate diamine for the 3-dimethylaminopropylamine used in Example 1 and repetition of the procedure detailed therein affords:
 1-benzyl-3-benzoyl-4-hydroxy-4-phenylpiperidine, melting at about 116°–118°C;
 1-(3-hexamethyleneiminopropyl)-3-benzoyl-4-hydroxy-4-phenylpiperidine;
 1-(2-pyrrolidinoethyl)-3-benzoyl-4-hydroxy-4-phenylpiperidine; and 1-(3-diisopropylaminopropyl)-3-benzoyl-4-hydroxy-4-phenylpiperidine.

EXAMPLE 6

A solution of aluminum hydride is prepared by mixing 30 parts by volume of 1.0 M lithium aluminum hydride in tetrahydrofuran with 1.47 parts of concentrated sulfuric acid at 0°C. After stirring at 0°C. for 45 minutes, 3.66 parts of 1-(3-dimethylaminopropyl)-3-benzoyl-4-hydroxy-4-phenylpiperidine dissolved in 17.6 parts of anhydrous tetrahydrofuran is added dropwise to this reaction mixture. Stirring at 0°C. is continued for an additional 1.5 hours. The reaction mixture is then decomposed by the addition of the following: 2 parts water in 3.5 parts of tetrahydrofuran; 3 parts by volume of 25% aqueous sodium hydroxide; and 3 parts water. The mixture is filtered and the salts washed with tetrahydrofuran. The tetrahydrofuran washings are combined, dried over anhydrous magnesium sulfate, and stripped of solvent under reduced pressure to give a white solid. The resulting white solid is recrystallized from carbon tetrachloride and washed with cold anhydrous ethyl ether to give white crystals. These white crystals are successively recrystallized from a chloroform-n-hexane mixture, and ethyl acetate, to give 1-(3-dimethylaminopropyl)-3-(α-hydroxybenzyl)-4-hydroxy-4-phenylpiperidine, melting at 142°–142.5°C. This compound is represented by the following structural formula

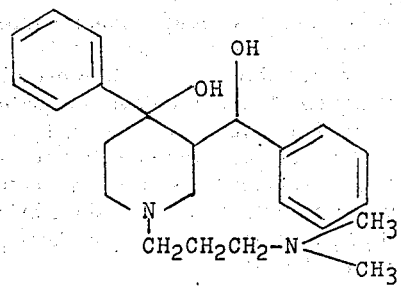

EXAMPLE 7

5.0 Parts of 1-(3-diethylaminopropyl)-3-benzoyl-4-hydroxy-4-phenylpiperidine is disssolved in 39.4 parts of ethanol and warmed to about 50°C. To this is slowly added 2.4 parts of sodium borohydride, and the reaction mixture heated to reflux for 0.5 hour. The reaction mixture is cooled to room temperature over a period of 2 hours and then poured into water. The resulting white precipitate is filtered and recrystallized from ethyl ether and methanol to give 1-(3-diethylaminoprpyl)-3-(α-hydroxybenzyl)-4-hydroxy-4-phenylpiperidine, melting at about 163°–165°C.

EXAMPLE 8

9.6 Parts of 1-(3-piperidinopropyl)-3-benzoyl-4-hydroxy-4-phenylpiperidine is dissolved in approximately 80 parts by volume of a 50% aqueous ethanol solution in a Parr Shaker. 1.0 Part of palladium catalyst is added and the mixture is shaken at 64°C. and a pressure of 50 psi for approximately 50.5 hours or until one molecular equivalent of hydrogen has been absorbed. The catalyst is removed by filtration and the filtrate is concentrated under reduced pressure to give an oil. The oil is dissolved in water and the soluton made alkaline with potassium carbonate. The resulting precipitate is filtered and recrystallized with an ethanol-ethyl ether mixture. The hydrochloride salt is obtained by dissolving this solid in isopropanol and adding a solution of hydrogen chloride in isopropanol. The resulting salt is separated by filtration to afford 1-(3-piperidinopropyl)-3-(α-hydroxybenzyl)-4-hydroxy-4-phenylpiperidine dihydrochloride, displaying a melting point of 208°–211°C. and represented by the following structural formula

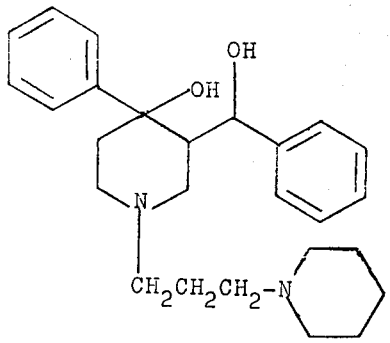
· 2HCl

EXAMPLE 9

10.0 Parts of 1-(2-dimethylaminoethyl)-3-benzoyl-4-hydroxy-4-phenylpiperidine is dissolved in 70 parts of ethanol. To this solution is slowly added 10.0 parts of sodium borohydride and the mixture heated to about 50°C. for ½ hour. After cooling to room temperature, the reaction mixture is poured into water. The resulting mixture is extracted three times with ethyl ether and the extracts are combined, dried over magnesium sulfate, and stripped of solvent under reduced pressure to give an oil. This oil is dissolved in ether and n-hexane added to the point of cloudiness. Cooling and filtration of the resulting crystals affords 1-(2-dimethylaminoethyl)-3-(α-hydroxybenzyl)-4-hydroxy-4-phenylpiperidine, melting at 157°–158°C.

EXAMPLE 10

Substitution of an equivalent amount of the appropriate 1-(substituted-aminoalkyl)-3-benzoyl-4-hydroxy-4-phenylpiperidine for the 1-(3-diethylaminopropyl)-3-benzoyl-4-hydroxy-4-phenylpiperidine of Example 7 and substantial repetition of the procedure detailed therein affords:

1-benzyl-3-(α-hydroxybenzyl)-4-hydroxy-4-phenylpiperidine, melting at about 153°–154°C;
1-(3-hexamethyleneiminopropyl)-3-(α-hydroxybenzyl)-4-hydroxy-4-phenylpiperidine;
1-(2-pyrrolidinoethyl)-3-(α-hydroxybenzyl)-4-hydroxy-4-phenylpiperidine; and
1-(3-diisopropylaminopropyl)-3-(α-hydroxybenzyl)-4-hydroxy-4-phenylpiperidine.

What is claimed is:
1. A compound of the formula

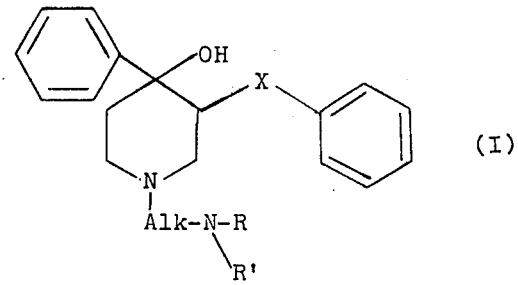

(I)

wherein X is hydroxymethylene or keto; Alk is alkylene of 2 to 6 carbon atoms, separating the nitrogen atoms attached thereto by at least 2 carbon atoms; and NRR' is selected from the group consisting of di(lower alkyl)amino, pyrrolidino, piperidino, and hexamethyleneimino.

2. A compound according to claim 1 which is 1-(3-dimethylaminopropyl)-3-benzoyl-4-hydroxy-4-phenylpiperidine.

3. A compound according to claim 1 which is 1-(3-diethylaminopropyl)-3-benzoyl-4-hydroxy-4-phenylpiperidine.

4. A compound according to claim 1 which is 1-(3-piperidinopropyl)-3-benzoyl-4-hydroxy-4-phenylpiperidine.

5. A compound according to claim 1 which is 1-(2-dimethylaminoethyl)-3-benzoyl-4-hydroxy-4-phenylpiperidine.

6. A compound according to claim 1 which is 1-(2-dimethylaminoethyl)-3-(α-hydroxybenzyl)-4-hydroxy-4-phenylpiperidine.

7. A compound according to claim 1 which is 1-(3-piperidinopropyl)-3-(α-hydroxybenzyl)-4-hydroxy-4-phenylpiperidine.

* * * * *